(12) United States Patent
Celeste et al.

(10) Patent No.: US 6,340,668 B1
(45) Date of Patent: Jan. 22, 2002

(54) NEURONAL USES OF BMP-11

(75) Inventors: Anthony J. Celeste; John M. Wozney, both of Hudson; R. Scott Thies, Andover, all of MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 09/414,234

(22) Filed: Oct. 7, 1999

Related U.S. Application Data

(63) Continuation of application No. 08/966,297, filed on Nov. 7, 1997, now abandoned, which is a continuation of application No. 08/919,850, filed on Aug. 12, 1997, which is a continuation-in-part of application No. 08/452,772, filed on May 30, 1995, now Pat. No. 5,700,911, which is a division of application No. 08/247,907, filed on May 20, 1994, now Pat. No. 5,639,638, which is a continuation-in-part of application No. 08/061,464, filed on May 12, 1993, now abandoned.

(51) Int. Cl.[7] .......................... A61K 38/18; C07K 14/51
(52) U.S. Cl. ...................... 514/12; 530/350; 424/198.1
(58) Field of Search ........................ 514/12; 530/350; 424/198.1

(56) References Cited

U.S. PATENT DOCUMENTS

| | | | |
|---|---|---|---|
| 4,737,578 A | 4/1988 | Evan et al. | 530/350 |
| 4,798,885 A | 1/1989 | Mason et al. | 530/350 |
| 5,071,834 A | 12/1991 | Burton et al. | 514/12 |
| 5,089,396 A | 2/1992 | Mason et al. | 435/69.1 |
| 5,102,807 A | 4/1992 | Burger et al. | 436/518 |
| 5,166,190 A | 11/1992 | Mather et al. | 514/8 |
| 5,208,219 A | 5/1993 | Ogawa et al. | 514/12 |
| 5,215,893 A | 6/1993 | Mason et al. | 435/69.1 |

FOREIGN PATENT DOCUMENTS

| | | |
|---|---|---|
| EP | 0 222 491 | 10/1986 |
| EP | 0 512 844 A1 | 5/1992 |
| WO | WO 87/00528 | 1/1987 |
| WO | WO 91/10444 | 7/1991 |
| WO | WO 92/14481 | 9/1992 |
| WO | WO 94/03200 | 2/1994 |
| WO | WO 94/21681 | 9/1994 |
| WO | WO 96/01845 | 1/1996 |
| WO | WO 97/34626 | 9/1997 |

OTHER PUBLICATIONS

Ogawa et al., J. Biol. Chem. 267(20):14233–36 (Jul. 15, 1992).
Schubert et al., Nature 344:868–870 (Apr. 26, 1990).
Bowie et al., Science 247:1306–10 (1990).
Wozney et al., J. Cell Science (Supp) 13:149–156 (1990).
Burt, Biochem Biophys Res Comm 184:590–595 (1992).
Lyons et al., PNAS (USA) 86:4554–4558 (1989).
Wozney et al., Science 242:1528–1534 (1988).
Border et al., J. Clin Invest 90:1–7 (1992).
Parker et al., J. Biol. Chem. 271:8161–9 (1996).
Rabin et al., Molecular and Cellular Biol., 13:2203–13 (1993).
Pollock, J. Biological Chem., 271:8008–14 (1996).
Mark, J. Cell Biol., 130:701–10 (1995).
Iwasaki, J. Biological chem., 271:17360–5 (1996).
Alberts et al., Molecular Biology of the Cell, 1994, Grand Publishing, Inc., New York, NY.
Bowie et al., Deciphering the message in protein sequences: tolerance to amino acid substitutions. Science, (Mar. 16, 1990) 247 (4948) 1306–10.
Kingsley D M. The TGF–beta superfamily: new members, new receptors, and new genetic tests of function in different organisms. Genes and Development (Jan. 1994) 8(2) 133–46.
Shah M; Foreman D M; Ferguston M W. Neutralisation of TGF–beta 1 and TGF–beta 2 or exogenous addition of TGF–beta 3 to cutaneous rat wounds reduces scarring. J. Cell Sci., (Mar. 1995) 108 (Pt 3) 985–1002.

*Primary Examiner*—David Romeo
(74) *Attorney, Agent, or Firm*—Ellen J. Kapinos; Barbara Gyure

(57) ABSTRACT

Purified BMP-11 proteins and processes for producing them are disclosed. Recombinant DNA molecules encoding the BMP-11 proteins are also disclosed. The proteins may be useful in regulating follicle stimulating hormone, such as for contraception. In addition, the proteins may be useful for the induction and/or maintenance of bone, cartilage and/or other connective tissue, and/or neuronal tissue.

2 Claims, No Drawings

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 789 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Bos Taurus
      (B) STRAIN: Bovine Activin WC (ix) FEATURE:
      (A) NAME/KEY: CDS
      (B) LOCATION: 324..704

(ix) FEATURE:
      (A) NAME/KEY: misc_feature
      (B) LOCATION: 322..323
      (D) OTHER INFORMATION: /note= "putative 3' end of intron"

(ix) FEATURE:
      (A) NAME/KEY: mat_peptide
      (B) LOCATION: 375..701

(xi) SEQUENCE DESCRIPTION: SEQ ID NO: 1:

```
AAACTGTATT TTGGGGTGAA GGTGTGAGTT AATAGATTCA CGGGACAACA AAGATGGGCT      60

GTTGTTGAGA CCTTGGGCCA AGGGGCTGAT GAGGGTCAGG TTGCCAAGAG AGAGAGAATT     120

AGGGAAGGTG AGTTTAGGGA GACATGGCTA GCTGGCAAGA AAAGTGGGTA GAAAACAGGG     180
```

```
GTTGGGGAGG GGAGCACTGG AGAAGCTCAG AAATCACTTG GTCTCTGTTC TCCTGCCCCT      240

ACTGAGGGGC AGGTGAGAAG AAACAGGGAG TAGGAGCTCC TCGAGGCTCT ATTACATCTC      300

TTTCTCCTCT CCCTCACCCC CAG CAT CCT TTT ATG GAG CTT CGA GTC CTA          350
                         His Pro Phe Met Glu Leu Arg Val Leu
                         -17     -15                     -10

GAG AAC ACA AAA CGG TCC CGG CGG AAC CTG GGC CTG GAC TGC GAT GAA        398
Glu Asn Thr Lys Arg Ser Arg Arg Asn Leu Gly Leu Asp Cys Asp Glu
            -5                   1               5

CAT TCA AGT GAG TCC CGC TGT TGC CGC TAC CCC CTC ACT GTG GAC TTT        446
His Ser Ser Glu Ser Arg Cys Cys Arg Tyr Pro Leu Thr Val Asp Phe
        10              15                  20

GAG GCT TTT GGC TGG GAC TGG ATC ATC GCT CCT AAA CGC TAC AAG GCC        494
Glu Ala Phe Gly Trp Asp Trp Ile Ile Ala Pro Lys Arg Tyr Lys Ala
25              30                  35                      40

AAC TAC TGC TCC GGC CAG TGC GAG TAC ATG TTT ATG CAA AAG TAT CCG        542
Asn Tyr Cys Ser Gly Gln Cys Glu Tyr Met Phe Met Gln Lys Tyr Pro
                45                  50                  55

CAC ACC CAC TTG GTG CAA CAG GCT AAC CCA AGA GGC TCT GCG GGG CCC        590
His Thr His Leu Val Gln Gln Ala Asn Pro Arg Gly Ser Ala Gly Pro
            60                  65                  70

TGC TGC ACA CCC ACC AAG ATG TCC CCA ATC AAC ATG CTC TAC TTC AAT        638
Cys Cys Thr Pro Thr Lys Met Ser Pro Ile Asn Met Leu Tyr Phe Asn
        75                  80                  85

GAC AAG CAG CAG ATT ATC TAC GGC AAG ATC CCT GGC ATG GTG GTG GAT        686
Asp Lys Gln Gln Ile Ile Tyr Gly Lys Ile Pro Gly Met Val Val Asp
90                  95                  100

CGC TGT GGC TGC TCC TAAGGTGGGG GACAGCGGAT GCCTCCCCAA CAGACCCTGC        741
Arg Cys Gly Cys Ser
105             110

CCCTAGACTC CCCCAGCCCT GACCCCCTGC TCCCCGGCCC TAGAGCTC                   789

(2) INFORMATION FOR SEQ ID NO: 2:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO: 2:

His Pro Phe Met Glu Leu Arg Val Leu Glu Asn Thr Lys Arg Ser Arg
-17     -15                     -10                 -5

Arg Asn Leu Gly Leu Asp Cys Asp Glu His Ser Ser Glu Ser Arg Cys
1               5                   10                      15

Cys Arg Tyr Pro Leu Thr Val Asp Phe Glu Ala Phe Gly Trp Asp Trp
                20                  25                      30

Ile Ile Ala Pro Lys Arg Tyr Lys Ala Asn Tyr Cys Ser Gly Gln Cys
            35                  40                  45

Glu Tyr Met Phe Met Gln Lys Tyr Pro His Thr His Leu Val Gln Gln
        50                  55                  60

Ala Asn Pro Arg Gly Ser Ala Gly Pro Cys Cys Thr Pro Thr Lys Met
    65                  70                  75

Ser Pro Ile Asn Met Leu Tyr Phe Asn Asp Lys Gln Gln Ile Ile Tyr
80                  85                  90                      95

Gly Lys Ile Pro Gly Met Val Val Asp Arg Cys Gly Cys Ser
                100                 105
```

(2) INFORMATION FOR SEQ ID NO: 3:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo Sapiens
        (B) STRAIN: Human Activin WC (ix) FEATURE:
        (A) NAME/KEY: CDS
        (B) LOCATION: 28..183

(ix) FEATURE:
        (A) NAME/KEY: misc_feature
        (B) LOCATION: 184..185
        (D) OTHER INFORMATION: /note= "two-thirds of codon at end of partial clone"

(xi) SEQUENCE DESCRIPTION: SEQ ID NO: 3:

```
TCTAGATGCT CCGGCCAGTG CGAGTAC ATG TTC ATG CAA AAA TAT CCG CAT                51
                              Met Phe Met Gln Lys Tyr Pro His
                               1               5

ACC CAT TTG GTG CAG CAG GCC AAT CCA AGA GGC TCT GCT GGG CCC TGT              99
Thr His Leu Val Gln Gln Ala Asn Pro Arg Gly Ser Ala Gly Pro Cys
 10              15                  20

TGT ACC CCC ACC AAG ATG TCC CCA ATC AAC ATG CTC TAC TTC AAT GAC             147
Cys Thr Pro Thr Lys Met Ser Pro Ile Asn Met Leu Tyr Phe Asn Asp
 25              30                  35                  40

AAG CAG CAG ATT ATC TAC GGC AAG ATC CCT GGC ATG GTGGTGGATC                  193
Lys Gln Gln Ile Ile Tyr Gly Lys Ile Pro Gly Met
                 45                  50

GCTGTGGCTG CTCCGGATCC                                                       213
```

(2) INFORMATION FOR SEQ ID NO: 4:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Phe Met Gln Lys Tyr Pro His Thr His Leu Val Gln Gln Ala Asn
 1               5                  10                  15

Pro Arg Gly Ser Ala Gly Pro Cys Cys Thr Pro Thr Lys Met Ser Pro
                 20                  25                  30

Ile Asn Met Leu Tyr Phe Asn Asp Lys Gln Gln Ile Ile Tyr Gly Lys
             35                  40                  45

Ile Pro Gly Met
     50
```

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: primer C to Bovine Activin WC (ix) FEATURE:
    (A) NAME/KEY: misc_feature
    (B) LOCATION: 1..9
    (D) OTHER INFORMATION: /note= "Restriction site for XbaI"

(xi) SEQUENCE DESCRIPTION: SEQ ID NO: 5:

TAGTCTAGAT GCTCCGGCCA GTGCGAGTAC                                    30

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Primer D to Bovine Activin WC (ix) FEATURE:
        (A) NAME/KEY: misc_feature
        (B) LOCATION: 1..9
        (D) OTHER INFORMATION: /note= "Restriction site for BamHI"

(xi) SEQUENCE DESCRIPTION: SEQ ID NO: 6:

TGCGGATCCG GAGCAGCCAC AGCGATCCAC                                    30

(2) INFORMATION FOR SEQ ID NO: 7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: DNA inserted into pMT2 CXM (xi) SEQUENCE DESCRIPTION: SEQ ID NO: 7:

CATGGGCAGC TCGAG                                                    15

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: DNA inserted into pMT21

(ix) FEATURE:
        (A) NAME/KEY: misc_feature
        (B) LOCATION: 1..6
        (D) OTHER INFORMATION: /note= "Pst restriction site"

(ix) FEATURE:
        (A) NAME/KEY: misc_feature
        (B) LOCATION: 15..26
        (D) OTHER INFORMATION: /note= "Eco RI and XhoI restriction
            sites"

(xi) SEQUENCE DESCRIPTION: SEQ ID NO: 8:

```
CTGCAGGCGA GCCTGAATTC CTCGAGCCAT CATG                                    34
```

(2) INFORMATION FOR SEQ ID NO: 9:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Portion of the EMC virus leader sequence (x) PUBLICATION INFORMATION:
        (A) AUTHORS: Jung, S K
        (C) JOURNAL: J. Virol.
        (D) VOLUME: 63
        (F) PAGES: 1651-1660
        (G) DATE: 1989

(xi) SEQUENCE DESCRIPTION: SEQ ID NO: 9:

```
CGAGGTTAAA AAACGTCTAG GCCCCCCGAA CCACGGGGAC GTGGTTTTCC TTTGAAAAAC        60

ACGATTGC                                                                 68
```

(2) INFORMATION FOR SEQ ID NO: 10:

(i) SEQUENCE CHARACTERISTICS:
        (A) LENGTH: 1270 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Human BMP-11

(vii) IMMEDIATE SOURCE:
        (B) CLONE: FB30.5

(ix) FEATURE:
        (A) NAME/KEY: CDS
        (B) LOCATION: 1..1086

(ix) FEATURE:
        (A) NAME/KEY: mat_peptide
        (B) LOCATION: 760..1086

(xi) SEQUENCE DESCRIPTION: SEQ ID NO: 10:

```
GAG CGC TCC AGC CGG CCA GCC CCG TCC GTG GCG CCC GAG CCG GAC GGC          48
Glu Arg Ser Ser Arg Pro Ala Pro Ser Val Ala Pro Glu Pro Asp Gly
-253          -250              -245              -240

TGC CCC GTG TGC GTT TGG CGG CAG CAC AGC CGC GAG CTG CGC CTA GAG          96
Cys Pro Val Cys Val Trp Arg Gln His Ser Arg Glu Leu Arg Leu Glu
          -235              -230              -225

AGC ATC AAG TCG CAG ATC TTG AGC AAA CTG CGG CTC AAG GAG GCG CCC         144
Ser Ile Lys Ser Gln Ile Leu Ser Lys Leu Arg Leu Lys Glu Ala Pro
     -220              -215              -210

AAC ATC AGC CGC GAG GTG GTG AAG CAG CTG CTG CCC AAG GCG CCG CCG         192
Asn Ile Ser Arg Glu Val Val Lys Gln Leu Leu Pro Lys Ala Pro Pro
-205              -200              -195              -190

CTG CAG CAG ATC CTG GAC CTA CAC GAC TTC CAG GGC GAC GCG CTG CAG         240
Leu Gln Gln Ile Leu Asp Leu His Asp Phe Gln Gly Asp Ala Leu Gln
              -185              -180              -175

CCC GAG GAC TTC CTG GAG GAG GAC GAG TAC CAC GCC ACC ACC GAG ACC         288
Pro Glu Asp Phe Leu Glu Glu Asp Glu Tyr His Ala Thr Thr Glu Thr
```

-continued

```
                 -170                -165                -160
GTC ATT AGC ATG GCC CAG GAG ACG GAC CCA GCA GTA CAG ACA GAT GGC       336
Val Ile Ser Met Ala Gln Glu Thr Asp Pro Ala Val Gln Thr Asp Gly
            -155                -150                -145

AGC CCT CTC TGC TGC CAT TTT CAC TTC AGC CCC AAG GTG ATG TTC ACA       384
Ser Pro Leu Cys Cys His Phe His Phe Ser Pro Lys Val Met Phe Thr
        -140                -135                -130

AAG GTA CTG AAG GCC CAG CTG TGG GTG TAC CTA CGG CCT GTA CCC CGC       432
Lys Val Leu Lys Ala Gln Leu Trp Val Tyr Leu Arg Pro Val Pro Arg
-125                -120                -115                -110

CCA GCC ACA GTC TAC CTG CAG ATC TTG CGA CTA AAA CCC CTA ACT GGG       480
Pro Ala Thr Val Tyr Leu Gln Ile Leu Arg Leu Lys Pro Leu Thr Gly
                -105                -100                 -95

GAA GGG ACC GCA GGG GGA GGG GGA GGC CGG CGT CAC ATC CGT ATC           528
Glu Gly Thr Ala Gly Gly Gly Gly Gly Arg Arg His Ile Arg Ile
             -90                 -85                 -80

CGC TCA CTG AAG ATT GAG CTG CAC TCA CGC TCA GGC CAT TGG CAG AGC       576
Arg Ser Leu Lys Ile Glu Leu His Ser Arg Ser Gly His Trp Gln Ser
         -75                 -70                 -65

ATC GAC TTC AAG CAA GTG CTA CAC AGC TGG TTC CGC CAG CCA CAG AGC       624
Ile Asp Phe Lys Gln Val Leu His Ser Trp Phe Arg Gln Pro Gln Ser
         -60                 -55                 -50

AAC TGG GGC ATC GAG ATC AAC GCC TTT GAT CCC AGT GGC ACA GAC CTG       672
Asn Trp Gly Ile Glu Ile Asn Ala Phe Asp Pro Ser Gly Thr Asp Leu
-45                 -40                 -35                 -30

GCT GTC ACC TCC CTG GGG CCG GGA GCC GAG GGG CTG CAT CCA TTC ATG       720
Ala Val Thr Ser Leu Gly Pro Gly Ala Glu Gly Leu His Pro Phe Met
             -25                 -20                 -15

GAG CTT CGA GTC CTA GAG AAC ACA AAA CGT TCC CGG CGG AAC CTG GGT       768
Glu Leu Arg Val Leu Glu Asn Thr Lys Arg Ser Arg Arg Asn Leu Gly
         -10                  -5                   1

CTG GAC TGC GAC GAG CAC TCA AGC GAG TCC CGC TGC TGC CGA TAT CCC       816
Leu Asp Cys Asp Glu His Ser Ser Glu Ser Arg Cys Cys Arg Tyr Pro
          5                  10                  15

CTC ACA GTG GAC TTT GAG GCT TTC GGC TGG GAC TGG ATC ATC GCA CCT       864
Leu Thr Val Asp Phe Glu Ala Phe Gly Trp Asp Trp Ile Ile Ala Pro
 20                  25                  30                  35

AAG CGC TAC AAG GCC AAC TAC TGC TCC GGC CAG TGC GAG TAC ATG TTC       912
Lys Arg Tyr Lys Ala Asn Tyr Cys Ser Gly Gln Cys Glu Tyr Met Phe
                 40                  45                  50

ATG CAA AAA TAT CCG CAT ACC CAT TTG GTG CAG CAG GCC AAT CCA AGA       960
Met Gln Lys Tyr Pro His Thr His Leu Val Gln Gln Ala Asn Pro Arg
             55                  60                  65

GGC TCT GCT GGG CCC TGT TGT ACC CCC ACC AAG ATG TCC CCA ATC AAC      1008
Gly Ser Ala Gly Pro Cys Cys Thr Pro Thr Lys Met Ser Pro Ile Asn
         70                  75                  80

ATG CTC TAC TTC AAT GAC AAG CAG CAG ATT ATC TAC GGC AAG ATC CCT      1056
Met Leu Tyr Phe Asn Asp Lys Gln Gln Ile Ile Tyr Gly Lys Ile Pro
     85                  90                  95

GGC ATG GTG GTG GAT CGC TGT GGC TGC TCT TAAGGTGGGG GATAGAGGAT        1106
Gly Met Val Val Asp Arg Cys Gly Cys Ser
100                 105

GCCTCCCCCA CAGACCCTAC CCCAAGACCC CTAGCCCTGC CCCCATCCCC CCAAGCCCTA   1166

GAGCTCCCTC CACTCTTCCC GCGAACATCA CACCGTTCCC CGACCAAGCC GTGTGCAATA   1226

CAACAGAGGG AGGCAGGTGG GAATTGAGGG TGAGGGGTTT GGGG                    1270
```

(2) INFORMATION FOR SEQ ID NO: 11:

-continued (i) SEQUENCE CHARACTERISTICS:
    (A) LENGTH: 362 amino acids
    (B) TYPE: amino acid
    (D) TOPOLOGY: linear (ii) MOLECULE TYPE: protein (xi) SEQUENCE DESCRIPTION: SEQ ID NO: 11:

```
Glu Arg Ser Ser Arg Pro Ala Pro Ser Val Ala Pro Glu Pro Asp Gly
-253         -250             -245             -240

Cys Pro Val Cys Val Trp Arg Gln His Ser Arg Glu Leu Arg Leu Glu
        -235             -230             -225

Ser Ile Lys Ser Gln Ile Leu Ser Lys Leu Arg Leu Lys Glu Ala Pro
        -220             -215             -210

Asn Ile Ser Arg Glu Val Val Lys Gln Leu Leu Pro Lys Ala Pro Pro
-205             -200             -195             -190

Leu Gln Gln Ile Leu Asp Leu His Asp Phe Gln Gly Asp Ala Leu Gln
                -185             -180             -175

Pro Glu Asp Phe Leu Glu Glu Asp Glu Tyr His Ala Thr Thr Glu Thr
                -170             -165             -160

Val Ile Ser Met Ala Gln Glu Thr Asp Pro Ala Val Gln Thr Asp Gly
            -155             -150             -145

Ser Pro Leu Cys Cys His Phe His Phe Ser Pro Lys Val Met Phe Thr
        -140             -135             -130

Lys Val Leu Lys Ala Gln Leu Trp Val Tyr Leu Arg Pro Val Pro Arg
-125             -120             -115             -110

Pro Ala Thr Val Tyr Leu Gln Ile Leu Arg Leu Lys Pro Leu Thr Gly
                -105             -100             -95

Glu Gly Thr Ala Gly Gly Gly Gly Gly Arg Arg His Ile Arg Ile
                -90              -85              -80

Arg Ser Leu Lys Ile Glu Leu His Ser Arg Ser Gly His Trp Gln Ser
        -75              -70              -65

Ile Asp Phe Lys Gln Val Leu His Ser Trp Phe Arg Gln Pro Gln Ser
        -60              -55              -50

Asn Trp Gly Ile Glu Ile Asn Ala Phe Asp Pro Ser Gly Thr Asp Leu
-45              -40              -35              -30

Ala Val Thr Ser Leu Gly Pro Gly Ala Glu Gly Leu His Pro Phe Met
                -25              -20              -15

Glu Leu Arg Val Leu Glu Asn Thr Lys Arg Ser Arg Arg Asn Leu Gly
                -10              -5                1

Leu Asp Cys Asp Glu His Ser Ser Glu Ser Arg Cys Cys Arg Tyr Pro
    5                10               15

Leu Thr Val Asp Phe Glu Ala Phe Gly Trp Asp Trp Ile Ile Ala Pro
20               25               30               35

Lys Arg Tyr Lys Ala Asn Tyr Cys Ser Gly Gln Cys Glu Tyr Met Phe
                40               45               50

Met Gln Lys Tyr Pro His Thr His Leu Val Gln Gln Ala Asn Pro Arg
            55               60               65

Gly Ser Ala Gly Pro Cys Cys Thr Pro Thr Lys Met Ser Pro Ile Asn
        70               75               80

Met Leu Tyr Phe Asn Asp Lys Gln Gln Ile Ile Tyr Gly Lys Ile Pro
        85               90               95

Gly Met Val Val Asp Arg Cys Gly Cys Ser
100              105
```

NEURONAL USES OF BMP-11

This application is a continuation of application U.S. Ser. No. 08/966,297 filed Nov. 7, 1997, abandoned; which is a continuation of Ser. No. 08/919,850 filed Aug. 12, 1997; which is a continuation-in-part of application U.S. Ser. No. 08/452,772 filed May 30, 1995 and issued as U.S. Pat. No. 5,700,911; which is a divisional application of U.S. Ser. No. 08/247,907, filed May 20, 1994 and issued as U.S. Pat. No. 5,639,638 on Jun. 17, 1997; which is a continuation-in-part application of U.S. Ser. No. 08/061,464, filed on May 12, 1993, now abandoned.

BACKGROUND OF THE INVENTION

The present invention relates, inter alia, to a novel family of purified proteins designated BMP-11, DNA molecules encoding them, and processes for obtaining them. The inventors have previously designated the BMP-11 proteins as Activin WC. The BMP-11 proteins may be useful to induce bone and/or cartilage formation and in wound healing and tissue repair, or for augmenting the activity of other bone morphogenetic proteins. The BMP-11 proteins may also be useful to regulate the production of follicle stimulating hormone, for contraception, to promote neuronal cell survival, to stimulate hematopoiesis, and to suppress the development of gonadal tumors. U.S. Pat. No. 4,798,885 disclosed DNA encoding the prepro inhibin α and β chains. U.S. Pat. No. 5,071,834 discloses pharmaceutical compositions of activin with two beta$_B$ chains formulated in a pharmaceutically acceptable carrier. U.S. Pat. No. 5,102,807 discloses a purified inhibin protein which suppresses production of FSH without suppressing production of luteinizing hormone.

In addition, the BMP-11 proteins of the present invention are useful to modulate all aspects of neuronal cell development, particularly neuronal formation, growth, differentiation, proliferation, and especially neuronal maintenance.

SUMMARY OF THE INVENTION

BMP-11 protein is a member of the TGF-β superfamily of proteins. The TGF-β superfamily includes the family of proteins known as bone morphogenetic proteins (BMPs), as well as a group of proteins that are termed inhibin-β. As discussed further herein, when dimerized with another BMP-11 (homodimer), BMP-11 protein is expected to demonstrate BMP-11 activity, as further described herein, as may be measured in accordance with the assays described in the examples herein. When dimerized as a heterodimer with inhibin-α proteins or with other inhibin-β proteins, the inhibin-β/BMP-11 heterodimer is expected to demonstrate effects on the production of follicle stimulating hormone (FSH), as described further herein. It is further expected that, in homodimeric form or in heterodimeric form with another member of the bone morphogenetic protein family, BMP-11 will exhibit BMP activity, i.e., the ability to induce the formation of bone, cartilage and/or other connective tissue. Thus, depending upon the environment of BMP-11, it may form dimers which will demonstrate either activin or inhibin activity, or bone, cartilage and/or other connective tissue-inducing activity. Accordingly, BMP-11 activity is defined as the ability to regulate the production of FSH in the assay described at Example 8 herein, or the ability to induce the formation of bone, cartilage and/or other connective tissue in the assays described at Examples 5 to 7 herein, as well as to modulate cell development, particularly neuronal formation, growth, differentiation, proliferation, and especially neuronal maintenance (Example 9).

Proteins termed inhibins and activins are produced in the gonad and exist naturally in follicular fluid. These proteins act at the level of the anterior pituitary gland to inhibit (inhibins) or stimulate (activins) the release of follicle-stimulating hormone (FSH) [for reviews see, e.g., Ying, S.-Y., *Endocr. Rev.*, 9:267–293 (1988) or Ling, N. et al, *Vitamins and Hormones*, 44:1–46 (Academic Press 1988)]. Briefly, dimeric proteins comprised of one chain of inhibin α and one chain of inhibin β ($β_A$ or $β_B$) are termed inhibins and are characterized by their ability to inhibit the release of follicle stimulating hormone (FSH), while other dimeric proteins comprised of two chains of inhibin β ($β_A$ or $β_B$) are termed activins and are characterized by their ability to stimulate the release of follicle stimulating hormone (FSH) [see, e.g., Ling et al., *Nature*, 321:779–782 (1986) or Vale, et al., *Nature*, 321:776–779 (1986) or Mason et al., *Nature*, 318:659–663 (1985) or Forage et al., *Proc. Natl. Acad. Sci. USA*, 83:3091–3095 (1986)].

It is recognized that FSH stimulates the development of ova in mammalian ovaries (Ross et al., in Textbook of Endocrinology, ed. Williams, p. 355 (1981) and that excessive stimulation of the ovaries with FSH will lead to multiple ovulations. FSH is also important in testicular function. Thus, BMP-11, in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility these mammals. BMP-11, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. BMP-11 may also be useful for advancement of the onset of fertility in sexually immature mammals, so as to increase the lifetime reproductive performance of domestic animals such as cows, sheep and pigs. It is further contemplated that BMP-11 may be useful in promoting neuronal cell survival [see, e.g., Schubert et al., *Nature*, 344:868–870 (1990)], modulating hematopoiesis by inducing the differentiation of erythroid cells [see, e.g., Broxmeyer et al, *Proc. Natl. Acad. Sci. USA*, 85:9052–9056 (1988) or Eto et al, *Biochem. Biophys. Res. Comm.*, 142:1095–1103 (1987)], for suppressing the development of gonadal tumors [see, e.g., Matzuk et al., *Nature*, 360:313–319 (1992)] or for augmenting the activity of bone morphogenetic proteins [see, e.g., Ogawa et al., *J. Biol. Chem.*, 267:14233–14237 (1992)].

BMP-11 proteins may be further characterized by their ability to modulate the release of follicle stimulating hormone (FSH) in established in vitro bioassays using rat anterior pituitary cells as described [see, e.g., Vale et al, *Endocrinology*, 91:562–572 (1972); Ling et al., *Nature*, 321:779–782 (1986) or Vale et al., *Nature*, 321:776–779 (1986)]. It is contemplated that the BMP-11 protein of the invention, when composed as a homodimer or a heterodimer with other inhibin β chains will exhibit stimulatory effects on the release of follicle stimulating hormone (FSH) from anterior pituitary cells as described [Ling et al., *Nature*, 321:779–782 (1986) or Vale et al., *Nature*, 321:776–779 (1986)]. Additionally, it is contemplated that the BMP-11 protein of the invention, when composed as a heterodimer with the inhibin a chain, will inhibit the release of follicle stimulating hormone (FSH) from anterior pituitary cells as described [see, e.g., Vale et al, *Endocrinology*, 91:562–572

(1972). Therefore, depending on the particular composition, it is expected that the BMP-11 protein of the invention may have contrasting and opposite effects on the release of follicle stimulating hormone (FSH) from the anterior pituitary.

Activin A (the homodimeric composition of inhibin $\beta_A$) has been shown to have erythropoietic-stimulating activity [see e.g. Eto et al., *Biochem. Biophys. Res. Commun.*, 142:1095–1103 (1987) and Murata et al., *Proc. Natl. Acad. Sci. U.S.A.*, 85:2434–2438 (1988) and Yu et al., *Nature*, 330:765–767 (1987)]. It is contemplated that the BMP-11 protein of the invention has a similar erythropoietic-stimulating activity. This activity of the BMP-11 protein may be further characterized by the ability of the BMP-11 protein to demonstrate erythropoietin activity in the biological assay performed using the human K-562 cell line as described by [Lozzio et al., *Blood*, 45:321–334 (1975) and U.S. Pat. No. 5,071,834].

The structures of several proteins, designated BMP-1 through BMP-9, have previously been elucidated. The unique inductive activities of these proteins, along with their presence in bone, suggests that they are important regulators of bone repair processes, and may be involved in the normal maintenance of bone tissue. The BMP-11 protein of the present invention is related to the above BMP proteins, and is expected to share BMP activities such as the ability to induce bone, cartilage and/or other connective tissue, such as tendon or ligament, and wound healing activities of the BMPs. In addition, it is expected that the proteins of the invention may act in concert with or perhaps synergistically with other related proteins and growth factors. Further therapeutic methods and compositions of the invention therefore comprise a therapeutic amount of at least one BMP-11 protein of the invention with a therapeutic amount of at least one of the other BMP proteins disclosed in co-owned patents and applications described below. Such combinations may comprise separate molecules of the BMP proteins or heteromolecules comprised of different BMP moieties. Further, BMP-11 proteins may be combined with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-α and TGF-β), and K-fibroblast growth factor (KFGF), parathyroid hormone (PTH), leukemia inhibitory factor (LIF/HILDA/DIA), insulin-like growth factors (IGF-I and IGF-II). Portions of these agents may also be used in compositions of the present invention.

The bovine BMP-11 DNA sequence (SEQ ID NO: 1) and amino acid sequence (SEQ ID: 2) and human BMP-11 DNA sequence (SEQ ID NO:10) and amino acid sequence (SEQ ID NO:11) are set forth in the Sequence Listings herein. Activin proteins are capable of regulating the production of follicle-stimulating hormone (FSH), and thus BMP-11 may be useful as a contraceptive or a fertility inducing therapeutic. In homodimeric form or in heterodimers with proteins of the inhibin-β group, purified BMP-11 protein is expected to demonstrate activin activity, and may be used to stimulate FSH. In addition, it is expected that the purified BMP-11 protein may be useful for the induction of bone, cartilage and/or other connective tissue.

Bovine BMP-11 may be produced by culturing a cell transformed with a DNA sequence comprising nucleotide #375 to nucleotide #704 as shown in SEQ ID NO: 1 and recovering and purifying from the culture medium a protein characterized by the amino acid sequence comprising amino acid #1 to #109 as shown in SEQ ID NO: 2 substantially free from other proteinaceous materials with which it is co-produced.

Human BMP-11 is expected to be homologous to bovine BMP-11. The invention, therefore, includes methods for obtaining the DNA sequences encoding human BMP-11, the DNA sequences obtained by these methods, and the human protein encoded by these DNA sequences. This method entails utilizing the bovine BMP-11 nucleotide sequence or portions thereof to design probes to screen libraries for the human gene or fragments thereof using standard techniques. A DNA sequence encoding part of the human BMP-11 protein (SEQ ID NO: 3) and the corresponding amino acid sequence (SEQ ID NO: 4) are set forth in the Sequence Listing. These sequences may also be used in order to design probes to obtain the complete human BMP-11 gene through standard techniques. Human BMP-11 may be produced by culturing a cell transformed with the BMP-11 DNA sequence and recovering and purifying BMP-11 from the culture medium. The purified expressed protein is substantially free from other proteinaceous materials with which it is co-produced, as well as from other contaminants.

The recovered purified protein is contemplated to demonstrate the ability to regulate the production of FSH. The proteins of the invention may be further characterized by the ability to regulate the production of follicle stimulating hormone (FSH) in established in vitro bioassays using rat anterior pituitary cells. BMP-11 proteins may also be characterized by the ability to induce the formation of bone, cartilage and/or other connective tissue, for,example, in the rat bone formation assay described below. They are also useful to modulate cell development, particularly neuronal formation, growth, differentiation, proliferation, and especially neuronal maintenance.

Another aspect of the invention provides pharmaceutical compositions containing a therapeutically effective amount of a BMP-11 protein in a pharmaceutically acceptable vehicle or carrier. BMP-11 compositions of the invention may be useful for the regulation of follicle stimulating hormone, and may be useful in contraception. Compositions of the invention may further include at least one other therapeutically useful agent such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, and BMP-10, disclosed in co-pending patent application Ser. No. 08/061,695, filed on May 12, 1993 presently abandoned, but cited in the corresponding application WO94/26893. The BMP-11 compositions may also be useful for a number of uses involving regulation of the production of follicle stimulating hormone, including contraception. These methods, according to the invention, entail administering to a patient needing such treatment, an effective amount of BMP-11.

The compositions of the invention may comprise, in addition to a BMP-11 protein, other members of the inhibin-β group of proteins or inhibin-α proteins, as well as otner therapeutically useful agents including growth factors such as epidermal growth factor (EGF), fibroblast growth factor (FGF), transforming growth factor (TGF-α and TGF-β), and insulin-like growth factor (IGF).

The BMP-11 compositions of the present invention may also be useful for treating a number of bone and/or cartilage defects, periodontal disease and various types of wounds. These methods, according to the invention, entail administering to a patient needing such bone and/or cartilage formation wound healing or tissue repair, an effective amount of a BMP-11 protein. These methods may also entail the administration of a protein of the invention in conjunction with at least one of the novel BMP proteins disclosed in the co-owned patents and applications described above. In addition, these methods may also include the administration of a BMP-11 protein with other growth factors including EGF, FGF, TGF-α, TGF-β, and IGF.

Still a further aspect of the invention are DNA sequences coding for expression of a BMP-11 protein. Such sequences include the sequence of nucleotides in a 5' to 3' direction illustrated in SEQ ID NO: 1 or DNA sequences which hybridize under stringent conditions with the DNA sequence of SEQ ID NO: 1 and encode a protein having BMP-11 activity. Finally, allelic or other variations of the sequences of SEQ ID NO: 1, whether such nucleotide changes result in changes in the peptide sequence or not, are also included in the present invention.

Still a further aspect of the invention are DNA sequences coding for expression of a BMP-11 protein. Such sequences include the sequence of nucleotides in a 5' to 3' direction illustrated in SEQ ID NO: 1 or SEQ ID NO:10, and DNA sequences which, but for the degeneracy of the genetic code, are identical to the DNA sequence of SEQ ID NO: 1 or SEQ ID NO:10, and encode the protein of SEQ ID NO: 2 or SEQ ID NO:11. Further included in the present invention are DNA sequences which hybridize under stringent conditions with the DNA sequence of SEQ ID NO: 1 or SEQ ID NO:10 and encode a protein having BMP-11 activity. Finally, allelic or other variations of the sequences of SEQ ID NO: 1 or SEQ ID NO: 10, whether such nucleotide changes result in changes in the peptide sequence or not, but where the peptide sequence still has BMP-11 activity, are also included in the present invention.

A further aspect of the invention includes vectors comprising a DNA sequence as described above in operative association with an expression control sequence therefor. These vectors may be employed in a novel process for producing a BMP-11 protein of the invention in which a cell line transformed with a DNA sequence encoding a BMP-11 protein in operative association with an expression control sequence therefor, is cultured in a suitable culture medium and a BMP-11 protein is recovered and purified therefrom. This process may employ a number of known cells both prokaryotic and eukaryotic as host cells for expression of the polypeptide.

The present invention also includes the use of the DNA sequences and vectors of the invention in gene therapy applications. In such use, the vectors may be transfected into the cells of a patient in vitro, and the cells may be reintroduced into a patient. Alternatively, the vectors may be introduced into a patient in vivo through targeted transfection.

Other aspects and advantages of the present invention will be apparent upon consideration of the following detailed description and preferred embodiments thereof.

DESCRIPTION OF THE SEQUENCES

SEQ ID NO:1 is a partial nucleotide sequence of the bovine BMP-11 encoding the mature bovine BMP-11 olypeptide.

SEQ ID NO:2 is the amino acid sequence of a partial propeptide and the complete mature bovine BMP-11 polypeptide, encoded by SEQ ID NO:1.

SEQ ID NO:3 is a partial nucleotide sequence of human BMP-11.

SEQ ID NO:4 is a partial amino acid sequence for human BMP-11 polypeptide encoded by SEQ ID NO:3.

SEQ ID NO:5 and 6 are primers to bovine BMP-11 used to isolate the human BMP-11 or other BMP-11 proteins.

SEQ ID NO:7 is a DNA sequence that is inserted into pMT2 CXM to add an XhoI recognition site near the SV40 origin of replication.

SEQ ID NO:8 is a DNA sequence inserted into pMT21 to insert an XhoI recognition site upstream from the DHFR gene.

SEQ ID NO:9 is a DNA sequence comprising a portion of the EMC virus leader sequence.

SEQ ID NO:10 is a DNA sequence encoding a partial propeptide and the complete mature human BMP-11 protein.

SEQ ID NO:11 is the amino acid sequence of a partial propeptide and the complete mature human BMP-11protein encoded by SEQ ID NO:10.

DETAILED DESCRIPTION OF THE INVENTION BMP-11

The bovine BMP-11 nucleotide sequence (SEQ ID NO: 1) and encoded amino acid sequence (SEQ ID NO: 2) and human BMP-11 nucleotide sequence (SEQ ID NO:10) and encoded amino acid sequence (SEQ ID NO:11) are depicted in the Sequence Listings herein. Purified bovine BMP-11 proteins of the present invention are produced by culturing a host cell transformed with a DNA sequence comprising the DNA coding sequence of SEQ ID NO: 1 from nucleotide #375 to #704 or the DNA coding sequence of SEQ ID NO: 10 from nucleotide #760 to #1086 and recovering and purifying from the culture medium a protein which contains the amino acid sequence or a substantially homologous sequence as represented by amino acids #1 to #109 of SEQ ID NO: 2 or amino acids 1 to 109 of SEQ ID NO: 11. For production of BMP-11 proteins in mammalian cells, the DNA sequence further comprises a suitable propeptide linked in frame with the above DNA coding sequences for BMP-11. The propeptide may be the native propeptide of BMP-11 or a propeptide from another member of the TGF-β superfamily The human BMP-11 sequence of the present invention is obtained using the whole or fragments of the bovine BMP-11 DNA sequence, or the partial human BMP-11 sequence of SEQ ID NO: 3 as a probe. Thus, the human BMP-11 DNA sequence comprise the DNA sequence of nucleotides #28 to #185 of SEQ ID NO: 3. The human BMP-11protein comprise the amino acid sequence of amino acids #1 to #52 of SEQ ID NO: 4.

It is expected that BMP-11, as expressed by mammalian cells such as CHO cells, exists as a heterogeneous population of active species of BMP-11 rotein with varying N-termini. It is expected that active species will comprise an amino acid sequence beginning at least with the cysteine residue at amino acid #6 of SEQ ID NO:1 or SEQ ID NO:10, or further in the N-terminal direction. Thus, it is expected that DNA sequences encoding active BMP-11 proteins will comprise nucleotides #375 or #390 to 701 of SEQ ID NO:1 or nucleotides #760 or #775 to #1086 of SEQ ID NO:10, and may comprise additional nucleotide sequence in the 5' direction of SEQ ID NO:1 or SEQ ID NO:10.

The N-terminus of human BMP-11 has been experimentally determined by expression in *E. coli* to be as follows: [M]NLGLDXDEHSSE corresponding to amino acids 1 to 12 of SEQ ID NO: 1 wherein X designates an amino acid residue with no clear signal, consistent with a location of cysteine at that position. Thus, it is expected that this species of BMP-11 will have an N-terminus at amino acid #1 of SEQ ID NO:1 or SEQ ID NO: 10, and DNA sequences encoding this species will comprise nucleotides #375 to #701 of SEQ ID NO:1 (bovine) or nucleotides #760 to 1086 of SEQ ID NO:10 (human). The apparent molecular weight of human BMP-11 monomer was determined by SDS-PAGE to be approximately 12 kd. The human BMP-11 protein exists as a clear, colorless solution in 0.1% trifluoroacetic acid.

The BMP-11 proteins recovered from the culture medium are purified by isolating them from other proteinaceous materials from which they are co-produced and from other contaminants present.

BMP-11 proteins may be characterized by the ability to regulate the production of FSH. BMP-11 proteins may further be characterized by the ability to modulate the release of follicle stimulating hormone (FSH) in established in vitro bioassays using rat anterior pituitary cells as described [see, e.g., Vale et al, *Endocrinology*, 91:562–572 (1972); Ling et al., *Nature*, 321:779–782 (1986) or Vale et al., *Nature*, 321:776–779 (1986)]. BMP-11 proteins may also be it characterized by the ability to induce the formation of bone, cartilage and/or other connective tissue. Such tissue-inducing activity of BMP-11 may further be characterized by the ability to induce the formation of bone, cartilage and/or other connective tissue in the assays described in the examples below.

The BMP-11 proteins provided herein also include factors encoded by the sequences similar to those of SEQ ID NO: 1 or SEQ ID NO:10, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO:2 or SEQ ID NO:11. These sequences, by virtue of sharing primary, secondary, or tertiary structural and conformational characteristics with inhibin-β polypeptides of SEQ ID NO:2 or SEQ ID NO:11 may possess BMP-11 activity in common therewith. Thus, they may be employed as biologically active substitutes for naturally-occurring BMP-11 polypeptides in therapeutic processes.

Other specific mutations of the sequences of BMP-11 proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. In addition, expression of the BMP-11 protein in bacterial cells results in non-glycosylated protein, without altering the glycosylation recognition sites.

The present invention also encompasses the novel DNA sequences, free of association with DNA sequences encoding other proteinaceous materials, and coding for expression of BMP-11 roteins. These DNA sequences include those depicted in SEQ ID NO:1 or SEQ ID NO:10 in a 5' to 3' direction and those sequences which hybridize thereto under stringent hybridization conditions, for example 0.1×SSC, 0.1% SDS at 65° C. [see, Maniatis et al, *Molecular Cloning (A Laboratory Manual)*, Cold Spring Harbor Laboratory (1982), pages 387 to 389] and encode a protein having BMP-11 activity. These DNA sequences also include those which comprise the DNA sequence of SEQ ID NO:3 and those which hybridize thereto under stringent hybridization conditions and encode a protein having BMP-11 activity.

Similarly, DNA sequences which code for BMP-11 proteins coded for by the sequences of SEQ ID NO:1 or SEQ ID NO:10, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO:1 or SEQ ID NO:10 which are caused by point mutations or by induced modifications (including insertion, deletion, and substitution) to enhance the activity, half-life or production of the polypeptides encoded are also encompassed in the invention.

Another aspect of the present invention provides a novel method for producing BMP-11 proteins. The method of the present invention involves culturing a suitable cell line, which has been transformed with a DNA sequence encoding a BMP-11 protein of the invention, under the control of known regulatory sequences. The transformed host cells are cultured and the BMP-11 proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kaufman et al, *Mol. Cell. Biol.*, 5(7): 1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis, Pseudomonas*, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel BMP-11 polypeptides. Preferably the vectors contain the full novel DNA sequences described above which encode the novel factors of the invention. Additionally, the vectors contain appropriate expression control sequences permitting expression of the BMP-11 protein sequences. Alternatively, vectors incorporating modified sequences as described above are also embodiments of the present invention. Additionally, the sequence of SEQ ID NO:1 or SEQ ID NO:10 or other sequences encoding BMP-11 proteins could be manipulated to express a mature BMP-11 by deleting BMP-11 encoding propeptide sequences and replacing them with sequences encoding the complete propeptides of other BMP proteins, activin proteins or other members of the TGF-β superfamily.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

For expression in mammalian host cells, the vector may comprise a coding sequence encoding a propeptide suitable for secretion of proteins by the host cell linked in proper reading frame to the coding sequence for mature BMP-11protein. Suitable propeptide encoding sequences may be obtained from DNA encoding proteins of the TGF-β superfamily of proteins, for example, including BMP-2 through BMP-9. For example, see U.S. Pat. No. 5,168,150, the disclosure of which is hereby incorporated by reference, in which a DNA encoding a precursor portion of a mammalian protein other than BMP-2 is fused to the DNA encoding a mature BMP-2 protein. Thus, the present invention includes chimeric DNA molecules comprising a DNA sequence encoding a propeptide from a member of the TGF-β superfamily of proteins linked in correct reading frame to a DNA sequence encoding a BMP-11 olypeptide. The term "chimeric" is used to signify that the propeptide originates from a different polypeptide than BMP-11.

A protein of the present invention, which regulates the production of FSH, has possible application in increasing fertility, when expressed in a composition as a homodimer or as a heterodimer with other proteins of the inhibin-β family. The proteins of the present invention may also be useful for contraception, when expressed in a composition as a heterodimer with proteins of the inhibin-α family.

A protein of the present invention, which induces cartilage and/or bone formation in circumstances where bone is not normally formed, has application in the healing of bone fractures and cartilage defects in humans and other animals. Such a preparation employing a BMP-11 protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-11 protein may be used in the treatment of periodontal disease, and in other tooth repair processes. Such agents may provide an environment to attract bone-forming cells, stimulate growth of bone-forming cells or induce differentiation of progenitors of bone-forming cells. BMP-11 polypeptides of the invention may also be useful in the treatment of osteoporosis. A variety of osteogenic, cartilage-inducing and bone inducing factors have been described. See, e.g., European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair). In addition, the BMP-11 proteins of the present invention are useful to modulate all aspects of neuronal cell development, particularly neuronal formation, growth, differentiation, proliferation, and especially neuronal maintenance.

The BMP-11 proteins of the invention induce neuronal cell formation and have application in the healing, protection, maintenance and/or repair of neuronal tissue. BMP-11 proteins are useful for a variety of neuronal defects including, for example, neuropathies, neurodegenerations, and nerve resection. These disorders can be associated with the cell body of the neuron (which can receive signals directly), with the axons of the neuron (which generally conducts signals away from the cell body), and/or with the dendrites of the neuron (which receive signals from the axons of other neurons). The branching of the axon allows for passage of a signal to many target cells simultaneously. Similarly, dendrites can be so extensively branched as to receive as many as 100,000 inputs on a single neuron. The immense variety in the pattern of branching of axons and dendrites is characteristic of different functional classes of neurons.

Neural tissue is classified as either peripheral or central. The central nervous system (CNS) comprises the brain and the spinal cord which is linked via the nerves to a large number of peripheral structures such as sense organs for input, and muscles and glands for output. Nerve cell clusters of the peripheral nervous system (PNS) are termed ganglia and are also connected via nerves to the central nervous system. All neural tissue, both peripheral and central, is made up of two major classes of cells: neurons and glial cells. Generally, once a neuron has reached maturity, it does not divide.

As a result, when a neuron dies, the resulting functional deficit is not typically repaired, and the resultant pathology is irreversible. Neuronal cell death can occur in neurodegenerative diseases, neuropathies and nerve resection.

Neuronal cell death occurs in neurodegenerative diseases such as Alzheimer's, Huntington's, Parkinson's and amyotrophic lateral sclerosis (ALS). These neurodegenerative diseases are each characterized by neuronal cell death in different areas of the CNS and can involve one or more types of neurons. For example, Parkinson's disease is characterized by the loss of dopaminergic neurons within the substantia nigra and locus cerulus, while ALS is asociated with the death of motor neurons. Strategies for treatment of neurodegenerative diseases include preventing neuronal death with neurotrophic agents, inducing neuronal regeneration in vivo with agents that affect endogenous stem cells, and cell replacement therapy with ex vivo manipulation of neural stem cells. BMP-11 may have applications in all of these therapy strategies in the prevention of neuronal death.

Peripheral neuropathy, including nerve resection, results from damage to neurons in the PNS. In this case, the neurons, once damaged, may or may not die. Typically, the axons of the neurons are affected, with destruction of the axon itself or the myelin sheath surrounding the axon. If the cell body of the neuron remains alive after axonal degeneration and/or demyelination, the neuron can sometimes repair itself. However, if the cell body dies, functional repair requires collateral nerve growth to compensate for the damage. Common causes of peripheral neuropathy include, for example, diabetes mellitus, chronic alchohol abuse, nutritional deficiencies (such as vitamins B and E), chronic renal failure, radiation therapy, HIV infection, and trauma or entrapment (like carpal tunnel syndrome) . Entrapment of neurons can occur when surrounding structures impinge on the neuron, e.g., as a result of inflammation in the area.

Peripheral neuropathy may be treated by agents which accelerate axonal repair, prevent neuronal death and induce collateral nerve growth. BMP-11 may be used in all of these treatments.

Nerve resection can occur during injury or trauma to the body and can also occur during surgical procedures such as when the nerve is accidentally cut. BMP-11 can be used to repair the breach. Alone, or in combination with other factors, that portion of the nerve which is severed, is maintained (kept from dying) until the severed connection has been restored.

BMP-11 can be used to promote the differentiation of stem cells into neuronal cells and can also be used to stimulate the production of axons and dendrites on both neurons that have not yet developed neurites, as well as on neurons that have lost these processes as a result of the aforementioned disorders.

A neural stem cell is a cell that gives rise to a variety of neurons and glial cells. Certain neurological diseases can be treated through ex vivo manipulation of neural stem cells for transplantation or in vivo activation of quiescent neural stem cells to produce healing from within. Advantage can be taken of regional differences in the nervous system to thereby affect neural stem cell behavior. Neurogenesis can be induced by BMP-11, alone, or in combination with other factors, and can convert neural stem cells into differentiated progeny. Other appropriate factors can also be provided along with the BMP-11for a stem cell to produce a particular neural or glial type.

Clinical trials show that neuron replacement therapies for neurodegenerative diseases, such as Parkinson's and Huntington's Disease, are feasible. Primary cells expanded in vitro can be used in neural grafting and results in the full integration of the grafted cells. In vitro expansion and manipulation of cells from the neural epithelium provide a range of well-characterized cells for transplant-based strategies for neural degenerative disease.

A further aspect of the invention comprises methods of treating neuronal tissue defects comprising applying a pharmaceutical composition comprising a BMP-11 protein, alone, or in combination with other factors, to a patient at a site of such defects, as well as methods for inducing the production of neuronal tissue comprising applying a pharmaceutical composition comprising BMP-11 protein to a patient in need of neuronal tissue production. Application of the composition may be by means of injection at the site, as well as implantation during surgery, or other application which will result in the BMP-11 protein exhibiting the desired effects. Such compositions may find use in protection or repair of neuronal tissue in various neuropathies, neurodegenerations, and nerve resection. For example, one method involves administration of a BMP-11 protein immediately at the time of trauma to thereby prevent cell death. Yet another method involves prophylactic administration of BMP-11 to patients having a genetic predisposition to neurodegenerative disorders.

A further aspect of the invention is a therapeutic method and composition for repairing fractures and other conditions related to cartilage and/or bone defects or periodontal diseases. The invention further comprises therapeutic methods and compositions for wound healing and tissue repair. Such compositions comprise a therapeutically effective amount of at least one of the BMP-11 proteins of the invention in admixture with a pharmaceutically acceptable vehicle, carrier or matrix.

Such a preparation employing a BMP-11 protein may also increase neuronal survival and therefore be useful in transplantation and treatment of conditions exhibiting a decrease in neuronal survival.

It is expected that the BMP-11 proteins of the invention may act in concert with or perhaps synergistically with other related proteins and growth factors. Further therapeutic methods and compositions of the invention therefore comprise a therapeutic amount of at least one BMP-11 rotein of the invention with a therapeutic amount of at least one of the BMP proteins or other growth factors disclosed in co-owned patents and applications described above. Such combinations may comprise separate molecules or heteromolecules comprised of different moieties. For example, a method and composition of the invention may comprise a disulfide linked dimer comprising a BMP-11 protein subunit and a subunit from an inhibin-$\alpha$ protein, an inhibin-$\beta$ protein or a BMP protein, such as BMP-1 through BMP-10. The agents useful with BMP-11 may include various growth factors such as epidermal growth factor (EGF), platelet derived growth factor (PDGF), transforming growth factors (TGF-$\alpha$ and TGF-$\beta$), and insulin-like growth factor (IGF). Further therapeutic methods and compositions of the invention comprise a therapeutic amount of at least one BMP-11 protein of the invention with a therapeutic amount of at least one of the BMP proteins disclosed in co-owned patents and applications described above. Such combinations may comprise separate molecules of the BMP proteins or heteromolecules comprised of different BMP moieties. For example, a method and composition of the invention may comprise a disulfide linked dimer comprising a BMP-11 protein subunit and a subunit from one of the "BMP" proteins described above. Thus, the present invention includes a purified BMP-11 olypeptide which is a heterodimer wherein one subunit comprises at least the amino acid sequence from amino acid #1 to amino acid #109 of SEQ ID NO:2 or SEQ ID NO:11, and one subunit comprises an amino acid sequence for a bone morphogenetic protein selected from the group consisting of BMP-1, BMP-2, BMP-3, BMP-4, BMP-5, BMP-6, BMP-7, BMP-8 and BMP-9. A further embodiment may comprise a heterodimer of BMP-11 moieties. Further, BMP-11 proteins may be combined with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-$\alpha$ and TGF-$\beta$), and k-fibroblast growth factor (kFGF), parathyroid hormone (PTH), leukemia inhibitory factor (LIF/HILDA/DIA), insulin-like growth factors (IGF-I and IGF-II). Portions of these agents may also be used in compositions of the present invention.

The BMP-11 proteins of the present invention may also be used in compositions combined with bone morphogenetic proteins. See for example, Ogawa et al., WO 92/14481 (1992); Ogawa et al., *J. Biol. Chem.*, 267:14233–14237 (1992). The bone morphogenetic proteins useful in such compositions include BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432; and BMP-10 disclosed in co-pending patent application Ser. No. 08/061,695, filed on May 12, 1993 presently abandoned, but cited in the corresponding application WO94/26893.

The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP and TGF proteins. Particularly domestic animals and thoroughbred horses in addition to humans are desired patients for such treatment with BMP-11 of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP-11 proteins which may also optionally be included in the composition as described above, may alternatively or additionally, be administered simultaneously or sequentially with the BMP-11 composition in the methods of the invention.

Preferably for bone, cartilage or other connective tissue formation, the composition includes a matrix capable of delivering BMP-11 or other BMP proteins to the site of tissue damage in need of repair, providing a structure for the developing bone and cartilage and optimally capable of being resorbed into the body. The matrix may provide slow release of BMP-11 and/or other bone inductive protein, as well as proper presentation and appropriate environment for cellular infiltration. Such matrices may be formed of materials presently in use for other implanted medical applications.

The choice of matrix material is based on biocompatibility, biodegradability, mechanical properties, cosmetic appearance and interface properties. The particular application of the BMP-11 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone, tendon or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Progress can be monitored by periodic assessment of bone growth and/or repair. The progress can be monitored, for example, x-rays, histomorphometric determinations and tetracycline labeling.

The dosage regimen will be determined by the attending physician considering various factors which modify the action of the BMP-11 protein, e.g. the patient's age, sex, and diet, the severity of any infection, time of administration and other clinical factors. The dosage may vary with the type of BMP protein or growth factor present in the composition. The dosage may also vary with the type of matrix used.

The following examples illustrate practice of the present invention in recovering and characterizing bovine BMP-11 protein and employing it to recover the human and other BMP-11 proteins, obtaining the human proteins and expressing the proteins via recombinant techniques. Also detailed are neuronal uses of BMP-11 proteins.

EXAMPLE 1

Bovine BMP-11

800,000 recombinants of a bovine genomic library constructed in the vector λEMBL3 are plated at a density of 8000 recombinant bacteriophage plaques per plate on 100 plates. Duplicate nitrocellulose replicas of the recombinant bacteriophage plaques are made from these plates and amplified. A fragment of human BMP-7 DNA corresponding to nucleotides #1081 to #1403 (FIG. 4, U.S. Pat. No. 5,141,905) is $^{32}$P-labelled by the random priming procedure of Feinberg et al. [Anal. Biochem. 132: 6–13 (1983)] and hybridized to one set of filters in standard hybridization buffer (SHB) (5×SSC, 0.170 SDS, 5×Denhardt's, 100 µg/ml Salmon sperm DNA) at 60° C. for 2 to 3 days. The filters are washed under reduced stringency conditions (4×SSC, 0.1% SDS at 60° C.). Multiple positively hybridizing recombinants are noted. 52 positively hybridizing recombinant bacteriophage plaques are selected and replated for secondaries. Duplicate nitrocellulose replicas of the recombinant plaques are made from these 52 secondary plates and amplified. One set of nitrocellulose filters is hybridized to the human BMP-7 DNA probe as described above and washed under the same reduced stringency conditions. The other set of filters is hybridized to a mixed BMP-5, BMP-6, and BMP-7 probe in SHB at 65° C. overnight and washed with a 0.1×SSC, 0.1% SDS at 65° C. (stringent hybridization and wash conditions). The mixed probe consists of relatively equal amounts of $^{32}$P-labelled DNA fragments comprising nucleotides #1452 to #2060 (FIG. 4, U.S. Pat. No. 5,106,748) of the human BMP-5 sequence, nucleotides #1395 to #1698 (FIG. 4, U.S. Pat. No. 5,187,076) of the human BMP-6 sequence, and nucleotides #1081 to #1403 (FIG. 4, U.S. Pat. No. 5,141,905) of the human BMP-7 sequence. The BMP-5, BMP-6 and BMP-7 DNA fragments are $^{32}$P-labelled by the random priming procedure and equal numbers of counts per minute (cpms) of each probe are combined and added to the SHB containing the other set of nitrocellulose filter replicas of the 52 secondary plates. 14 recombinants, which hybridized positively to the human BMP-7 probe under the reduced stringency conditions and exhibited weak or no hybridization to the mixed BMP-5/6/7 probe under high stringency conditions, are selected for further analysis. All 14 recombinants which exhibit these hybridization characteristics are plaque purified and bacteriophage DNA is prepared from each. The positively hybridizing region of one of the 14 recombinants exhibiting the hybridization characteristics described above, designated λ7r-30, is localized to a 0.5 kb SacI restriction fragment. This fragment is subcloned into a plasmid vector (pGEM-3) and DNA sequence analysis is performed. The partial DNA sequence (SEQUENCE ID NO. 1) and derived amino acid sequence (SEQUENCE ID NO. 2) of clone λ7r-30 are shown in the Sequence Listings.

The bacteriophage λ7r-30 has been deposited with the ATCC on Apr. 7, 1993, and accorded the accession number ATCC 75439. This deposit meets the requirements of the Budapest Treaty of the International Recognition of the Deposit of Microorganisms for the Purpose of Patent Procedures and regulations thereunder.

This λ7r-30 clone encodes at least a portion of the bovine BMP-11 protein of the present invention. The nucleotide sequence of clone λ7r-30 contains an open reading frame of 456 nucleotides #246–701 of SEQ ID NO:1. The nucleotide sequence of #324 to #701 of SEQ ID NO:1 defines an open reading frame of 378 nucleotides, encoding at least 126 amino acids of the C-terminal portion of a bovine BMP-11 protein, as determined by alignment to other BMP proteins and other proteins within the TGF-β family. The nucleotide sequence #246 to #323 defines an open reading frame contiguous with the sequence encoding the predicted 126 amino acid BMP-11 eptide, however a reduced degree of amino acid identity of the peptide deduced from this region of DNA sequence (#246 to #323) to other BMP proteins and other proteins of the TGF-β family and the presence of multiple potential splice acceptor consensus sequences make it difficult to define the 5' limit of this exon of the bovine BMP-11 gene. The presence of an in-frame stop codon at nucleotide positions #243 to #245 indicates that nucleotide sequence of clone λ7r-30 contains at least one exon/intron boundary of the bovine BMP-11 gene.

Based upon the knowledge of other proteins within the TGF-β family, it is predicted that the BMP-11 recursor polypeptide would be cleaved at the multibasic sequence ARG-SER-ARG-ARG corresponding to amino acids 1 through 12 of SEQ ID NO: 1 in agreement with a proposed consensus proteolytic processing sequence of ARG-X-X-ARG corresponding to amino acids −4 to −1 of SEQ ID NO: 1. Cleavage of the BMP-11 precursor polypeptide is expected to generate a 109 amino acid mature peptide beginning with the amino acid ASN at position #1. The processing of BMP-11 into the mature form is expected to involve dimerization and removal of the N-terminal region in a manner analogous to the processing of the related protein TGF-β [Gentry et al., *Molec. & Cell. Biol.*, 8:4162 (1988); Derynck et al., *Nature*, 316:701(1985)].

It is contemplated therefore that the mature active species of BMP-11 comprises a homodimer of two polypeptide subunits, each subunit comprising amino acids #1 to #109 with a predicted molecular weight of approximately 12,000 daltons. Further active species are contemplated comprising amino acids #6 to #109, thereby including the first conserved cysteine residue. As with other members of the TGF-β family of proteins, the carboxy-terminal region of the BMP-11 rotein exhibits greater sequence conservation than the more amino-terminal portion. The percent amino acid identity of the BMP-11 protein in the cysteine-rich C-terminal domain (amino acids #6 to #109) to the corresponding region of other proteins within the TGF-β family is as follows: BMP-2, 39%; BMP-3, 37%; BMP-4, 37%; BMP-5, 42%, BMP-6, 45%; BMP-7, 42%; BMP-8, 39%; BMP-9, 40%; Vg1, 39%; GDF-1, 34%; TGF-β1, 36%; TGF-β2, 38%; TGF-β3, 38%; inhibin β(B), 41%; inhibin β(A), 39%.

EXAMPLE 2

Human BMP-11

Bovine and human BMP-11 genes are presumed to be significantly homologous, therefore the bovine coding sequence or a portion thereof is used as a probe to screen a human genomic library or as a probe to identify a human cell line or tissue which synthesizes the analogous human protein. A human genomic library, such as Stratagene catalog #944201, may be screened with such a probe, and presumptive positives isolated and DNA sequence obtained. Evidence that this recombinant encodes a portion of the human BMP-11 relies on the bovine/human protein and gene structure homologies.

Once a recombinant bacteriophage containing DNA encoding a portion of the human BMP-11 molecule is obtained, the human coding sequence can be used as a probe to identify a human cell line or tissue which synthesizes BMP-11 mRNA. Alternatively, the bovine BMP-11 coding sequence can be used as a probe to identify such human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence of the bovine or human BMP-11. Alternatively, the bovine BMP-11 coding sequence is used to design oligonucleotide primers which will specifically amplify a portion of the BMP-11 encoding sequence located in the region located between the primers utilized to perform the specific amplification reaction. It is contemplated that bovine and human BMP-11 sequences would allow one to specifically amplify corresponding human BMP-11 encoding sequences from mRNA, cDNA or genomic DNA templates. Once a positive source has been identified by one of the above described methods, mRNA is selected by oligo (dT) cellulose chromatography and cDNA is synthesized and cloned in λgt10 or other λ bacteriophage vectors known to those skilled in the art. (i.e. λZAP) by established techniques (Toole et al., supra). It is also possible to perform the oligonucleotide primer directed amplification reaction, described above, directly on a pre-established human cDNA or genomic library which has been cloned into a A bacteriophage vector. In such cases, a library which yields a specifically amplified DNA product encoding a portion of human BMP-11 protein could be screened directly, utilizing the fragment of amplified BMP-11 encoding DNA as a probe.

Oligonucleotide primers designed on the basis of the DNA sequence of the bovine BMP-11 genomic clone λ7r-30 are predicted to allow the specific amplification of human BMP-11 encoding sequences. The following oligonucleotide primer is designed on the basis of nucleotides #501 to #521 of the DNA sequence set forth in SEQ ID NO. 1 and synthesized on an automated DNA synthesizer.

Primer C:
TAGTCTAGATGCTCCGGCCAGTGCGAGTAC(SEQ ID NO:5)

The first nine nucleotides of primer C (underlined) comprise the recognition sequence for the restriction endonuclease XbaI which can be utilized to facilitate the manipulation of a specifically amplified DNA sequence encoding the BMP-11 protein of the invention and are thus not derived from the DNA sequence presented in SEQ ID NO: 1.

The following oligonucleotide primer is designed on the basis of nucleotides #701 to #678 of the DNA sequence set forth in SEQ ID NO. 1 and synthesized on an automated DNA synthesizer:

Primer D:
TGCGGATCCGGAGCAGCCACAGCGATCCAC (SEQ ID NO:6)

The first nine nucleotides of primer D (underlined) comprise the recognition sequence for the restriction endonuclease BamHI which can be utilized to facilitate the manipulation of a specifically amplified DNA sequence encoding the BMP-11 protein of the invention and are thus not derived from the DNA sequence present in SEQ ID NO:1.

The standard nucleotide symbols in the above identified primers are as follows: A, adenosine; C, cytosine, G, guanine; and T, thymine.

Primers C and D identified above are utilized as primers to allow the amplification of a specific nucleotide from human genomic DNA. The amplification reaction is performed as follows:

Human genomic DNA (source: peripheral blood lymphocytes) is denatured at 100° C. for five minutes and then chilled on ice prior to addition to a reaction mixture containing 200 μW each deoxynucleotide triphosphates (dATP, dGTP, dCTP and dTTP) 10 mM Tris-HCl pH8.3, 50 mM KCl, 1.5 mM MgCl$_2$, 0.001% gelatin, 1.25 units Taq DNA polymerase, 100 pM oligonucleotide primer C and 100 pM oligonucleotide primer D. This reaction mixture is then subjected to thermal cycling in the following manner: 3 minutes at 94° C., 1 minute at 50° C., 1 minute at 72° C. for one cycle, then 1 minute at 94° C., 1 minute at 50° C., 1 minute at 72° C. for thirty-nine cycles.

The DNA which is specifically amplified by this reaction is separated from the excess oligonucleotide primers C and D utilized to initiate the amplification by the use of a DNA purification resin based protocol under the conditions suggested by the manufacturer. The resulting DNA product is digested with the restriction endonucleases XbaI and BamHI, phenol extracted, chloroform extracted. Buffer exchange and removal of small fragments of DNA resulting from the XbaI/BaHI restriction digest is accomplished by dilution of the digested DNA product in 10 Mm Tris-Hcl pH8.0, 1 Mm EDTA followed by centrifugation through a centricon™ 30 microconcentrator (W.R. Grace & Co., Beverly, Mass.; Product #4209). The resulting XbaI/BamHI digested amplified DNA product is subcloned into a plasmid vector (pBluescript) between the XbaI and BamHI restriction sites of the polylinker region. DNA sequence analysis of the resulting subclones indicates that the specifically amplified DNA sequence product encodes a portion of the human BMP-11 protein of this invention. The DNA sequence (SEQ ID NO:3) and derived amino acid sequence (SEQ ID NO:4) of this specifically amplified DNA fragment are set forth in the Sequence Listings.

Nucleotides #1 to #27 of this sequence comprise a portion of oligonucleotide primer C and nucleotides #186 to #213 comprise a portion of oligonucleotide primer D utilized to perform the specific amplification reaction. Due to the function of oligonucleotide primers C and D (designed on the basis of bovine BMP-11 DNA sequence) in initiating the amplification reaction, they may not correspond exactly to the actual sequence encoding a human BMP-11 and are therefore not translated in the above amino acid sequence derivation. The DNA sequence, from nucleotide #28 to #185 of SEQ ID NO: 3, or portions thereof, specifically amplified from the human genomic DNA template can be utilized as a probe to identify additional human BMP-11 encoding sequences from human genomic or human cDNA libraries by standard hybridization/screening techniques known to those skilled in the art.

One million, two hundred thousand recombinants of a human fetal brain cDNA library (Stratagene catalog #936206) constructed in the vector λZAPII are plated at a density of 24,000 recombinant bacteriophge plaques per plate on 50 plates. Duplicate nitrocellulose replicas of the recombinant bacteriophage plaques are made from these plates. An oligonucleotide probe designed on the basis of nucleotides #53–#82 of SEQ ID NO:3 is synthesized on an automated DNA synthesizer. This oligonucleotide probe is radioactively labelled with $\gamma^{32}$P-ATP and is hybridized to both sets of the duplicate nitrocellulose replicas in SHB at 65° C. Nine positively hybridizing recombinants are noted. One of the positively hybridizing recombinants, named λFB30.5, is plaque purified. Bacteriophage plate stocks of the purified λFB30.5 cDNA clone are prepared and bacteriophage DNA is isolated. A bacterial plasmid named FB30.5, generated by the in vivo excision protocol described by the supplier (Stratagene) and containing the entire insert of the λFB30.5 bacteriophage cDNA clone, has been deposited with the ATCC, 12301 Parklawn Drive, Rockville, Md. USA under the requirements of the Budapest Treaty and designated as ATCC #69619. A portion of the DNA sequence of clone FB30.5 is set forth in SEQ ID NO: 10.

One million recombinants of a human genomic library (Stratagene Catalog #944201) constructed in the vector λFIX are plated at a density of 20,000 recombinant bacteriophge plaques per plate on 50 plates. Duplicate nitrocellulose replicas of the recombinant bacteriophage plaques are made from these plates. An oligonucleotide probe designed on the basis of nucloetides #57–#86 of SEQ ID NO:10, with the exception of an inadvertent substitution of CkC for GCG at nucleotides #59–#61 of SEQ ID NO:10, is synthesized on an automated DNA synthesizer. This oligonucleotide probe is radioactively labelled with $\gamma^{32}$P-ATP and is hybridized to both sets of the duplicate nitrocellulose replicas in SHB at 65° C. Five positively hybridizing recombinants are noted. One of the positively hybridizing recombinants, named 30GEN.4,is plaque purified. Bacteriophage plate stocks of the purified 30GEN.4 genomic clone are prepared and bacteriophage DNA is isolated. A bacteriophage stock of this genomic clone has been deposited with the ATCC, 12301 Parklawn Drive, Rockville, Md. USA under the requirements of the Budapest Treaty and designated as ATCC #75775. A portion of the DNA sequence of clone 30GEN.4 is set forth in SEQ ID NO: 10. A portion of the DNA sequence of the genomic clone 30GEN.4 was determined to be identical to a portion of the DNA sequence of the cDNA clone FB30.5. The extent of this overlap (nucleotides #1–#198) of SEQ ID NO:10 were used as a basis to compile the partial coding sequence of the BMP-10 protein. The genomic clone 30GEN.4 is expected to contain additional 5' coding sequences of the human BMP-11 rotein which are expected to encode the remainder of the BMP-11 recursor polypeptide, including the initiator methionine. The partial sequence of human BMP-11 is presented in SEQ ID NO:10 and it should be noted that nucleotides #1–198 have been determined to be present in both the 30GEN.4 genomic clone and the FB30.5 cDNA clone while nucleotides #199–#1270 are derived entirely from the cDNA clone FB30.5. SEQ ID NO:10 predicts a human BMP11 precursor protein of at least 362 amino acids. Based on the knowledge of other BMPs and other proteins within the TGF-β family, it is predicted that the precursor polypeptide would be cleaved at the multibasic sequence ARG-SER-ARG-ARG (amino acids #−4 through #−1 of SEQ ID NO:11) in agreement with the proposed consensus proteolytic processing sequence ARG-X-X-ARG. Cleavage of the human BMP-11 precursor polypeptide at this location would generate a 109 amino acid mature peptide beginning with the amino acid ASN at position #1 of SEQ ID NO:11. The processing of human BMP-11 into the mature form is expected to involve dimerization and removal of the N-terminal region in a manner analogous to the procesing of the related protein TGF-β [L. E. Gentry, et al. Molec. & Cell. Biol. 8:4162 (1988); R.Derynck, et al., Nature 316:701 (1985). It is contemplated that the mature active species of human BMP-11 comprises a homodimer of two polypeptide subunits, each subunit comprising amino acids #1–#108 of SEQ ID NO:11, with a predicted molecular weight of 12,000 daltons. Further active species are contemplated comprising amino acids #7–#108 of SEQ ID NO:11, thereby including the first conserved cysteine residue. Heterodimeric molecules comprising one subunit of BMP-11 and another subunit of another member of the BMP/TGF-β superfamily are also contemplated.

EXAMPLE 3

Expression of BMP-11

In order to produce bovine, human or other mammalian BMP-11 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-11 is contemplated to be stably transformed mammalian cells.

One skilled in the art can construct mammalian expression vectors by employing the sequence of SEQ ID NO:1 or SEQ ID NO:10, or other DNA sequences encoding BMP-11 proteins or other modified sequences and known vectors, such as pCD [Okayama et al., Mol. Cell Biol., 2:161–170 (1982)], pJL3, pJL4 [Gough et al., EMBO J., 4:645–653 (1985)] and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Morinaga, et al., Biotechnology 84: 636 (1984). This removes bases 1075 to 1145 relative to the Hind III site near the SV40 origin of replication and enhancer sequences of pMT2. In addition it inserts the following sequence:

5' PO-CATGGGCAGCTCGAG-3' (SEQ ID NO:7)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2b1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. Coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'

```
                                          (SEQ ID NO: 8)
    5'-CTGCAGGCGAGCCTGAATTCCTCGAGCCATCATG -3'
         PstI         Eco RI XhoI
```

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung, et al, J. Virol 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

```
        5'-CGAAGGTTAAAAACGTCTAGGCCCCCCGAACCACGGGGACGTGGTTTTCCTTTGAAAAACACGATTGC -3'  (SEQ ID NO:9)
           TaqI                                                                XhoI
```

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-11 DNA sequences. For instance, BMP-11 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-11 proteins. Additionally, the sequence of SEQ ID NO:1 or SEQ ID NO:10 or other sequences encoding BMP-11 proteins could be manipulated to express a mature BMP-11 by deleting BMP-11 encoding propeptide sequences and replacing them with sequences encoding the complete propeptides of other BMP proteins, activin proteins or other members of the TGF-β superfamily.

One skilled in the art can manipulate the sequences of SEQ ID NO:1 or SEQ ID NO:10 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified BMP-11 coding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells and a BMP-11 protein expressed thereby. For a strategy for producing extracellular expression of BMP-11 proteins in bacterial cells, see, e.g. European patent application EPA 177,343.

Similar manipulations can be performed for the construction of an insect vector (See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-11 protein of the invention in mammalian cells may involve the construction of cells containing multiple copies of the heterologous BMP-11 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.,* 159:601–629 (1982). This approach can be employed with a number of different cell types.

For example, a plasmid containing a DNA sequence for a BMP-11 of the invention in operative association with other plasmid sequences enabling expression thereof and the DHFR expression plasmid pAdA26SV(A)3 [Kaufman and Sharp, *Mol. Cell. Biol.,* 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.,* 5:1750 (1983). Transformants are cloned, and biologically active BMP-11 expression is monitored by one or more of the BMP-11 activity assays described in Examples 5 to 8 below. BMP-11 expression should increase with increasing levels of MTX resistance. BMP-11 polypeptides are characterized using standard techniques known in the art such as pulse labeling with [35S] methionine or cysteine and polyacrylamide gel electrophoresis. Similar procedures can be followed to produce other related BMP-11 proteins.

EXAMPLE 4

Biological Activity of Expressed BMP-11

To measure the biological activity of the expressed BMP-11 proteins obtained in Example 3 above, the proteins are recovered from the cell culture and purified by isolating the BMP-11 proteins from other proteinaceous materials with which they are co-produced as well as from other contaminants. The purified protein may be assayed in accordance with the assays for BMP-11 activity described in Examples 5 to 8 below.

EXAMPLE 5

W-20 BIOASSAYS

A. Description of W-20 cells

Use of the W-20 bone marrow stromal cells as an indicator cell line is based upon the conversion of these cells to osteoblast-like cells after treatment with a BMP protein [Thies et al, *Journal of Bone and Mineral Research,* 5:305 (1990); and Thies et al, *Endocrinology,* 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 μl of media (DME with 10% heat inactivated fetal calf serum, 2 mM glutamine and 100 Units/ml penicillin+100 μg/ml streptomycin. The cells are allowed to attach overnight in a 95% air, 5% $CO_2$ incubator at 37° C.

The 200 μl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200 μl per well of calcium/magnesium free phosphate buffered saline and these washes are discarded.

50 μl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 μl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 μl of 0.2 N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, a standard curve of absorbance values is generated.

Absorbance values for known amounts of BMPs are determined and converted to μmoles of p-nitrophenol phosphate cleaved per unit time.

These values are then used to compare the activities of known amounts of BMP-11 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples, e.g., BMP-11, are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table I.

TABLE I

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

EXAMPLE 6
Rosen-Modified Sampath-Reddi Assay

A modified version of the rat bone formation assay described in Sampath and Reddi, *Proc. Natl. Acad. Sci. USA*, 80:6591–6595 (1983) is used to evaluate bone, cartilage and/or other connective tissue inductive activity of BMP-11 proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [see, Reddi et al, *Proc. Natl. Acad. Sci.*, 69:1601 (1972)].

The other half of each implant is fixed and processed for histological analysis. 1 µm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

The BMP-11 proteins of this invention may be assessed for activity in this assay.

EXAMPLE 7
Biological Activity of Expressed BMP-11

To measure the biological activity of the expressed BMP-11 proteins obtained in Example 3 above, the proteins are recovered from the cell culture and purified by isolating the BMP-11 proteins from other proteinaceous materials with which they are co-produced as well as from other contaminants. The purified protein may be assayed in accordance with the rat bone formation assay described in Example 6.

Purification is carried out using standard techniques known to those skilled in the art.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)].

EXAMPLE 8
Tests to Determine Activin Activity of BMP-11

Purification is carried out using standard techniques known to those skilled in the art. It is contemplated, as with other proteins of the TGF-β superfamily, that purification may include the use of Heparin sepharose.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)].

BMP-11 proteins may be further characterized by their ability to modulate the release of follicle stimulating hormone (FSH) in established in vitro bioassays using rat anterior pituitary cells as described in, for example, Vale et al, *Endocrinology,* 91:562–572 (1972); Ling et al., *Nature,* 321:779–782 (1986) or Vale et al., *Nature,* 321:776–779 (1986), the disclosures of which are hereby incorporated by reference. Alternatively, BMP-11 may be characterized by their ability to stimulate erythropoietin activity in the human K-562 cell line, as described by Lozzio et al., *Blood,* 45:321–334 (1975) and U.S. Pat. No. 5,071,834, at colimn 15, the disclosures of which are hereby incorporated by reference.

In addition, BMP-11 may be characterized by their activity in cell survival assays, as described in Schubert, *Nature,* 344:868–870 (1990), the disclosure of which is incorporated by reference.

EXAMPLE 9
Use of BMP-11 as a Neuronal Differentiation, Growth, and Maintenance Factor BMP-11 can be used to modulate all aspects of neuronal cell development, particularly neuronal formation, growth, differentiation, proliferation, and especially neuronal maintenance.

The survival of primary neurons or neuronal cell lines in culture, such as a PC12 neuronal cell line, is frequently used as an in vitro assay for identifying neurotrophic factors. PC12 cells are derived from a rat adrenal pheochromocytoma tumor, and are often used in culture to model peripheral sympathetic neurons. BMP-11 romotes survival of PC12 cells under serum-free conditions.

PC12 cells are plated at sub-confluence in 96 well plates with 10% fetal calf serum for 24 hrs, then switched to a serum-free medium with or without 200 ng/ml BMP-11, and cultured for 3–6 days. Cell survival is estimated by the addition of "CellTiter 96 Aqueous One Solution", an MTS-based product from Promega Corporation, to the treated PC12 cells for the last 3 hrs of the final treatment day. MTS is reduced to a colored formazan product by cellular NADH and NADPH from living cells. Formazan product is measured spectrophotometrically by absorbance at 490 nm using a standard microplate reader. As shown in Table II below, BMP-11 promotes PC12 cell survival.

TABLE II

MTS Reduction (Abs$^{490}$)

| Experiment | Days of Treatment | Control | 200 ng/ml BMP-11 |
|---|---|---|---|
| 1 | 3 | 0.543 ± 0.022 | 0.828 ± 0.049 |
| 2 | 4 | 0.143 ± 0.012 | 0.276 ± 0.021 |
| 3 | 6 | 0.039 ± 0.006 | 0.196 ± 0.019 |

(Values are means of replicate samples ± S.E.)

In addition to being used to characterize neuronal maintenance/survival factors, PC12 cells have also been used to identify neuronal differentiation factors based on morphological changes in the cells. When cultured under serum-free conditions, untreated PC12 cells appear spherical, while nerve growth factor (NGF) treated PC12 cells show the formation of neuronal processes or neurites. Thus, in another assay, PC12 cells are treated for 3 days with BMP-11 which results in neurite formation, as detected by phase contrast microscopy. BMP-11 therefore induces neuronal differentiation.

To further characterize the neuronal activities of BMP-11, BMP-11 is administered in vivo in animal models of peripheral neuropathy (Eliasson, "Nerve Conduction Changes in Experimental Diabetes," J. Clin. Invest. 43:2353–2358 (1964)), CNS neurodegeneration (Mitsumoto and Bradley, "Murine Motor Neuron Disease (the Wobbler Mouse). Degeneration and Regeneration of the Lower Motor Neuron," Brain 105:811–834 (1982)) (Steiner et al., "Neurotrophic Immunophilin Ligands Stimulate Structural and Functional Recovery in Neurodegenerative Animal Models," Proc. Nat'l. Acad. Sci. USA 94:2019–2024 (1997)), peripheral nerve resection (Erikkson et al., "BDNF and NT-3 Rescue Sensory But Not Motor Neurons Following Axotomy in the Neonate," Neuroreport 5:1445–1448 (1994)), and spinal nerve resection (Oudega and Hagg, "Nerve Growth Factor Promotes Regeneration of Sensory Axons into Adult Rat Spinal Cord," Exp. Neurol. 140:218–229 (1996)).

The BMP-11 roteins of the invention induce neuronal cell formation and protect, maintain, heal, and repair neuronal tissue in these disorders.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A method for promoting the survival of neuronal cells in a mammal comprising administering to said cells an amount of a bone morphogenetic protein-11 (BMP-11) effective to promote the survival of said cells, wherein said BMP-11 comprises an amino acid sequence selected from the group consisting of SEQ ID NO: 2 and SEQ ID NO: 11.

2. A method for promoting the survival neuronal cells in vitro comprising administering to said cells an amount of a bone morphogenetic protein-11 (BMP-11) effective to promote survival of said cells, wherein said BMP-11 comprises an amino acid sequence selected from the group consisting of SEQ ID NO: 2 and SEQ ID NO: 11.

* * * * *